(12) United States Patent
Pierrepont et al.

(10) Patent No.: US 12,023,101 B2
(45) Date of Patent: Jul. 2, 2024

(54) IMPLANT ALIGNMENT SYSTEM

(71) Applicant: Corin Limited, Cirencester (GB)

(72) Inventors: James William Pierrepont, Cromer (AU); Catherine Zoe Stambouzou, Cromer (AU); Jevan Arulampalam, Cammeray (AU)

(73) Assignee: Corin Limited (GB)

( * ) Notice: Subject to any disclaimer, the term of this patent is extended or adjusted under 35 U.S.C. 154(b) by 576 days.

(21) Appl. No.: 17/044,983

(22) PCT Filed: Apr. 4, 2019

(86) PCT No.: PCT/GB2019/050975
§ 371 (c)(1),
(2) Date: Oct. 2, 2020

(87) PCT Pub. No.: WO2019/193341
PCT Pub. Date: Oct. 10, 2019

(65) Prior Publication Data
US 2021/0145517 A1    May 20, 2021

(30) Foreign Application Priority Data
Apr. 4, 2018    (GB) .................................... 1805567

(51) Int. Cl.
*A61B 34/10*    (2016.01)
*A61B 90/00*    (2016.01)
(Continued)

(52) U.S. Cl.
CPC .............. *A61B 34/10* (2016.02); *A61B 90/37* (2016.02); *A61F 2/34* (2013.01); *A61F 2/3609* (2013.01);
(Continued)

(58) Field of Classification Search
CPC .............. A61B 34/10; A61B 2034/101; A61B 2034/102; A61B 2034/105; A61B 2034/107
See application file for complete search history.

(56) References Cited

U.S. PATENT DOCUMENTS

| | | |
|---|---|---|
| 6,205,411 B1 | 3/2001 | DiGioia, III et al. |
| 8,831,324 B2 | 9/2014 | Penenberg |

(Continued)

FOREIGN PATENT DOCUMENTS

| | | |
|---|---|---|
| AU | 2015223078 B2 | 2/2015 |
| WO | 2017124043 A1 | 1/2017 |
| WO | 2017106858 A1 | 6/2017 |

OTHER PUBLICATIONS

International Search Report dated Jul. 29, 2019 in International Application No. PCT/GB2019/050975.
(Continued)

*Primary Examiner* — Nicholas W Woodall
(74) *Attorney, Agent, or Firm* — Kim IP Law Group LLC

(57) ABSTRACT

A joint prosthesis and/or trial implant alignment system (10) for intraoperatively assisting an alignment of a joint prosthesis and/or trial implant (12) during a surgical procedure is disclosed. The system comprises patient-specific pre-operative data (14) forming a three-dimensional image (14) containing bone structure (32) and a predetermined alignment of the joint prosthesis and/or trial implant (12) thereon. A patient imaging device (16) is for producing patient-specific intraoperative data 18 which forms a two-dimensional image 18 showing bone structure (32) and a real-time position of the joint prosthesis and/or trial implant (12) thereon. Registration means (20) registers the intraoperative data 18 with the pre-operative data (14) based on geometry of said bone structure and/or geometry of said joint prosthesis and/or trial implant (12). A display device (22) for (Continued)

displaying an output of the registration means (20), thereby enabling a visual indication of the said real-time alignment of the joint prosthesis and/or trial implant (12) relative to the said predetermined alignment.

19 Claims, 3 Drawing Sheets

(51) Int. Cl.
    *A61B 90/35*     (2016.01)
    *A61F 2/34*     (2006.01)
    *A61F 2/36*     (2006.01)
    *A61F 2/38*     (2006.01)
    *A61F 2/40*     (2006.01)
    *A61F 2/46*     (2006.01)

(52) U.S. Cl.
    CPC .......... *A61F 2/3859* (2013.01); *A61F 2/3877* (2013.01); *A61F 2/389* (2013.01); *A61F 2/4014* (2013.01); *A61F 2/4081* (2013.01); *A61F 2/4684* (2013.01); *A61B 2090/376* (2016.02); *A61B 2090/378* (2016.02)

(56) References Cited

U.S. PATENT DOCUMENTS

| | | | |
|---|---|---|---|
| 8,876,830 B2 * | 11/2014 | Hodorek | A61B 17/155 606/88 |
| 2004/0167654 A1 | 8/2004 | Grimm et al. | |
| 2016/0100909 A1 | 4/2016 | Wollowick et al. | |
| 2016/0128654 A1 | 5/2016 | Wollowick et al. | |
| 2016/0287345 A1 | 6/2016 | Penenberg | |
| 2016/0338777 A1 | 11/2016 | Penenberg et al. | |
| 2017/0245942 A1 | 8/2017 | Penenberg et al. | |
| 2017/0258526 A1 * | 9/2017 | Lang | A61B 34/10 |
| 2019/0180466 A1 | 6/2019 | Tao | |

OTHER PUBLICATIONS

Written Opinion dated Jul. 29, 2019 in International Application No. PCT/GB2019/050975.

* cited by examiner

IMPLANT ALIGNMENT SYSTEM

CROSS-REFERENCE TO RELATED APPLICATIONS

This application is a U.S. national phase application under 35 U.S.C. § 371 of International Patent Application No. PCT/GB2019/050975, filed on Apr. 4, 2019, which claims priority to Great Britain Patent Application No. 1805567.3, filed Apr. 4, 2018, the disclosures of each of which are hereby incorporated by reference in their entirety for all purposes.

The present invention relates to a joint prosthesis and/or trial implant alignment system for intraoperatively assisting an alignment of a joint prosthesis and/or trial implant during a surgical procedure. The invention further relates to methods of intraoperatively assisting an alignment of a joint prosthesis, determining a joint implant alignment and monitoring an implant alignment, as well as an implant alignment determination system.

It can be necessary to implant a joint prosthesis, implant and/or trial implant into a patient. For example, if a joint of a patient becomes worn or damaged, at least part of the joint may need to be replaced. This requirement for replacement may particularly apply to hip, knee or shoulder joint replacements.

In order to ensure a best post-operative outcome for the patient, it can be necessary to predetermine an alignment, orientation and/or position of the prosthesis or implant relative to the patient's body. For example, it can be necessary to predetermine an orientation of an acetabular cup with respect to the patient's acetabulum before performing a total hip arthroplasty.

In this instance, after implanting the trial implant and/or prosthesis it would be necessary to verify that the implant has been correctly aligned with respect to the patient's body, to correspond with the predetermined alignment. If this is not done, the patient may have a prosthesis or trial implant implanted at a less than optimal alignment.

Currently, the alignment of the trial implant and/or prosthesis may be verified by eye or palpation intraoperatively by the surgeon, which can result in errors and/or failure to detect misalignment. Misalignment may result in the failure of the prosthesis and/or the requirement for revision surgery. The present invention seeks to provide a solution to these problems.

According to a first aspect of the present invention, there is provided a joint prosthesis and/or trial implant alignment system for intraoperatively assisting an alignment of a joint prosthesis and/or trial implant during a surgical procedure, the system comprising: patient-specific pre-operative data forming a three-dimensional image containing bone structure and a predetermined alignment of the joint prosthesis and/or trial implant thereon; a patient imaging device for intraoperatively imaging in two dimensions an operative area of the patient; patient-specific intraoperative data outputted from the patient imaging device forming a two-dimensional image showing bone structure and a real-time position of the joint prosthesis and/or trial implant thereon; registration means for registering the intraoperative data with the pre-operative data based on geometry of said bone structure and/or geometry of said joint prosthesis and/or trial implant; and a display device capable of intraoperatively displaying an output of the registration means, thereby enabling a visual indication of the said real-time alignment of the joint prosthesis and/or trial implant relative to the said predetermined alignment.

The registration means enables reliable intraoperative verification of a correspondence between the predetermined and real-time alignments of the joint prosthesis and/or trial implant. Such verification would not necessarily depend on the skill or experience of the surgeon, unlike manual verification via palpation and/or by eye. The display device enables this information to be displayed to the surgeon. The alignment system therefore prevents or limits the joint prosthesis or trial implant from being misaligned or implanted incorrectly. Alternatively, the system increases the likelihood of optimal implantation alignment. Therefore, the risk of impingement or other post-operative joint complications or issues is reduced. By having a three-dimensional pre-operative image, rather than a two-dimensional pre-operative image as may be known in the prior art, a pre-operative representation of the operative area can be manipulated. Therefore, intraoperatively, the patient can be imaged from any appropriate angle and the intraoperative image can be matched with the pre-operative representation. If the pre-operative data were a two-dimensional image, then the operative area would need to be intraoperatively imaged more precisely to allow a direct comparison between the two images. Therefore, the present invention allows for a greater flexibility in intraoperative imaging.

Preferably, the geometry of said bone structure and/or geometry of said joint prosthesis and/or trial implant may include at least one of a point, contour, profile, plane, line, curvature or radius. Identifying geometry via a point allows for identification with the images containing less of the operative area. Said geometry including a contour, profile, plane, line, curvature or radius increases the amount of registerable data and therefore increases the chance of accurate registration.

Advantageously, the registration means may include contouring determination means for determining contouring of at least one of bone structure, the joint prosthesis and trial implant in the patient-specific intraoperative data and/or patient-specific pre-operative data. Beneficially, the contouring determination means may be adapted to determine contouring of at least one of the bone structure, the joint prosthesis and trial implant in the two-dimensional image and/or three-dimensional image. Contour determination means enables contours of the images to be identified. Contours can be more easily and reliably identified on the images, and can be more unique to a given patient, than other geometries and so improves a success rate of registration.

Additionally, the registration means may include landmark designation means for designating a landmark of at least one of the bone structure, joint prosthesis, and trial implant which is common to both the patient-specific intraoperative data and patient-specific pre-operative data. Optionally, the landmark designation means may be adapted to designate at least one of the or a further landmark of bone structure, joint prosthesis and trial implant which is common to the two-dimensional image and three-dimensional image. In the event that the registration means is unable to register the two images together, for example if there are too many conflicting possible registration geometries, the landmark designation means effectively allows the surgeon or surgical personnel to assist with registration. This therefore increases the likelihood of successful registration and may prevent or limit the requirement to take repeat intraoperative images in an attempt to enable registration.

In a preferable embodiment, said output of the registration means may include the two-dimensional image superposed on the three-dimensional image or vice versa. The two and three-dimensional images superposed with each other enables a clear indication of any discrepancies between the real-time and predetermined alignments. This also indicates the direction and magnitude of adjustment required.

Preferably, said output of the registration means may include real-time orientation and/or positioning numerical data of the joint prosthesis and/or trial implant relative to the bone structure and/or the predetermined alignment. Values of the real-time alignment, particularly when provided in combination with values of the predetermined alignment, allow for the surgeon to expeditiously, and without requiring significant additional visual analysis, verify the correspondence of the alignments.

Advantageously, said output of the registration means may include at least one indicator to indicate a direction and/or magnitude of adjustment to the joint prosthesis and/or trial implant to correspond with the said predetermined alignment. Indicators, such as arrows, allow the surgeon to clearly identify the required adjustment.

Alternatively, said output of the registration means may include a real-time or pseudo-real-time three-dimensional image produced from a combination of at least part of the patient-specific intraoperative data and/or patient-specific pre-operative data. The pseudo-real-time three-dimensional image is considered to be "pseudo-real-time" given that it is not a directly imaged three-dimensional image. The two-dimensional image provides the relative positions of the implant and bone structure and, given the known dimensions of the implant and the bone structure, a three-dimensional image can be predicted, constructed or generated. The real-time three-dimensional images can enable the surgeon to clearly identify the real-time alignment of the implant.

Beneficially the patient imaging device includes at least one of a fluoroscope, X-ray machine, ultrasound, PACS or Therapy Imaging and Model Management System.

Preferably, the joint prosthesis and/or trial implant alignment system further comprises a wired or wireless data connection between the patient imaging device and the registration means for transferring the patient-specific intraoperative data to the registration means. The wired or wireless data connection enables fast and/or automatic transferal of the intraoperative data to the registration means.

Optionally, the joint prosthesis and/or trial implant alignment system further comprises a secondary imaging device for producing an intermediate copy of said two-dimensional image for transferal to the registration means. This prevents or limits the requirement for the registration means and the imaging device to be compatible and/or directly connectable.

Advantageously, the patient-specific pre-operative data may be at least in part outputted from at least one of single-plane X-ray, multi-plane X-ray, magnetic resonance imaging, computer tomography, ultrasound or statistical shape modelling. Direct imaging of the patient allows for the three-dimensional image to more accurately reflect the bone structure of the patient. Therefore, an optimal alignment and better post-operative results are possible. Statistical shape modelling prevents or limits the requirement to directly image each patient and therefore may save time and/or limit radiation dosage to patients.

In a preferable embodiment, the predetermined alignment of the joint prosthesis and/or trial implant may be based on patient-specific information which is indicative of one or more dynamic characteristics and post-implant activities preference data. This enables a patient-specific alignment to be determined which may reduce the chance of impingement of the joint and/or the requirement for revision surgery.

Preferably, the joint prosthesis and/or trial implant includes an acetabular cup, acetabular cup liner, femoral head, femoral stem, screws, bolts; femoral, tibial and patellar components of a total knee replacement prosthesis; humeral head, glenoid component and/or custom prosthesis and/or trial implant.

According to a second aspect of the present invention, there is provided a method of intraoperatively assisting an alignment of a joint prosthesis and/or trial implant, the method comprising the steps: a] pre-operatively predetermining a required alignment of a joint prosthesis and/or trial implant on a bone structure; b] pre-operatively acquiring three-dimensional first image data corresponding to an operative area of the patient and which includes said bone structure and the said predetermined required position of the joint prosthesis and/or trial implant thereon; c] intraoperatively positioning the joint prosthesis and/or trial implant on actual bone structure of the patient; d] intraoperatively acquiring two-dimensional second image data of the operative area of the patient relating to said actual bone structure and a real-time position of the joint prosthesis and/or trial implant thereon; e] intraoperatively registering the three-dimensional first image data with the two-dimensional second image data or vice versa based on at least one of bone structure geometry, joint prosthesis and trial implant geometry; and f] displaying to surgical personnel a visual indication of the said real-time alignment of the joint prosthesis and/or trial implant relative to the said predetermined required alignment.

According to a third aspect of the present invention, there is provided a method of determining a joint implant alignment, the method comprising the steps of: a] obtaining three-dimensional image data of a bone structure from a first source; b] forming a three-dimensional image of the bone structure using the three-dimensional image data; c] locating a representation of a first joint implant in a required alignment on the three-dimensional image; d] obtaining two-dimensional image data of the or a further bone structure with a second joint implant thereon from a second source which is different to the first source; and e] registering the three-dimensional image data and the two-dimensional image data based on geometry of said bone structure and/or geometry of said joint implant to determine whether an alignment of the said second joint implant matches or substantially matches the required alignment of the said first joint implant.

According to a fourth aspect of the present invention there is provided a method of monitoring an implant alignment, the method comprising the steps of: a] obtaining three-dimensional image data of a bone structure from a first source; b] forming a three-dimensional image of the bone structure using the three-dimensional image data; c] locating a representation of a first joint implant in a required alignment on the three-dimensional image; d] obtaining two-dimensional image data of the or a further bone structure with a second joint implant thereon from a second source which is different to the first source; and e] registering the three-dimensional image data and the two-dimensional image data based on geometry of said bone structure and/or geometry of said joint implant to determine whether an alignment of the said second joint implant matches or substantially matches the required alignment of the said first joint implant.

According to a fifth aspect of the present invention there is provided a method of monitoring a trial-implant alignment, the method comprising the steps of: a] obtaining three-dimensional image data of a bone structure from a first source; b] forming a three-dimensional image of the bone structure using the three-dimensional image data; c] locating a representation of a first joint implant in a required alignment on the three-dimensional image; d] obtaining two-dimensional image data of the or a further bone structure with a second joint implant thereon from a second source which is different to the first source; and e] registering the three-dimensional image data and the two-dimensional image data based on geometry of said bone structure and/or geometry of said joint implant to determine whether an alignment of the said second joint implant matches or substantially matches the required alignment of the said first joint implant.

According to a sixth aspect of the present invention there is provided an implant alignment determination system comprising: three-dimensional image-data acquisition means for acquiring three-dimensional image data of a bone structure; three-dimensional image-generation means for generating a three-dimensional image of the bone structure from the said three-dimensional image data; first implant-location means for locating a first implant in a required alignment on the said three-dimensional image; two-dimensional image-data acquisition means for acquiring two-dimensional image data of a or the bone structure with a second implant thereon; and registration means for registering the three-dimensional image data and the two-dimensional image data based on bone structure geometry and/or implant geometry to determine whether an alignment of the said second implant matches or substantially matches the required alignment of the said first implant.

According to a seventh aspect of the present invention there is provided a joint prosthesis and/or trial implant alignment system for intraoperatively assisting an alignment of a joint prosthesis and/or trial implant during a surgical procedure, the system comprising: patient-specific pre-operative data forming a three-dimensional image containing bone structure; a patient imaging device for intraoperatively imaging in two dimensions an operative area of the patient; patient-specific intraoperative data outputted from the patient imaging device forming a two-dimensional image showing bone structure and a real-time position of the joint prosthesis and/or trial implant thereon; registration means for registering the intraoperative data with the pre-operative data based on geometry of said bone structure and/or geometry of said joint prosthesis and/or trial implant; and a display device capable of intraoperatively displaying an output of the registration means, thereby enabling a visual indication of the said real-time alignment of the joint prosthesis and/or trial implant relative to the bone structure in the three-dimensional image.

The system enables visual indication and verification of the real-time alignment of the joint prosthesis and/or trial implant in the intraoperative data on the three-dimensional image, which is far more comprehensive than in a two-dimensional environment. Thus, the surgeon can check the positioning of the alignment of joint prosthesis and/or trial implant in a three-dimensional environment at any appropriate angle.

According to an eighth aspect of the present invention there is provided a method of intraoperatively assisting an alignment of a joint prosthesis and/or trial implant, the method comprising the steps: a] pre-operatively acquiring three-dimensional first image data corresponding to an operative area of the patient and which includes said bone structure; b] intraoperatively positioning the joint prosthesis and/or trial implant on actual bone structure of the patient; c] intraoperatively acquiring two-dimensional second image data in two dimensions of the operative area of the patient relating to said actual bone structure and a real-time position of the joint prosthesis and/or trial implant thereon; d] intraoperatively registering the three-dimensional first image data with the two-dimensional second image data or vice versa based on at least one of bone structure geometry, joint prosthesis and trial implant geometry; and e] displaying to surgical personnel a visual indication of the said real-time alignment of the joint prosthesis and/or trial implant relative to the bone structure in the three-dimensional first image data.

According to a ninth aspect of the present invention there is provided a method of determining a joint implant alignment, the method comprising the steps of: a] obtaining three-dimensional image data of a bone structure from a first source; b] forming a three-dimensional image of the bone structure using the three-dimensional image data; c] obtaining two-dimensional image data of the or a further bone structure with a joint implant thereon from a second source which is different to the first source; and d] registering the three-dimensional image data and the two-dimensional image data based on geometry of said bone structure and/or geometry of said joint implant to determine an alignment of the said joint implant with the three-dimensional image of the bone structure.

According to a tenth aspect of the present invention there is provided a method of monitoring an implant alignment, the method comprising the steps of: a] obtaining three-dimensional image data of a bone structure from a first source; b] forming a three-dimensional image of the bone structure using the three-dimensional image data; c] obtaining two-dimensional image data of the or a further bone structure with a joint implant thereon from a second source which is different to the first source; and d] registering the three-dimensional image data and the two-dimensional image data based on geometry of said bone structure and/or geometry of said joint implant to determine an alignment of the said joint implant with the three-dimensional image of the bone structure.

According to an eleventh aspect of the present invention there is provided a method of monitoring a trial-implant alignment, the method comprising the steps of: a] obtaining three-dimensional image data of a bone structure from a first source; b] forming a three-dimensional image of the bone structure using the three-dimensional image data; c] obtaining two-dimensional image data of the or a further bone structure with a joint implant thereon from a second source which is different to the first source; and d] registering the three-dimensional image data and the two-dimensional image data based on geometry of said bone structure and/or geometry of said joint implant to determine an alignment of the said joint implant with the three-dimensional image of the bone structure.

According to a twelfth aspect of the present invention there is provided an implant alignment determination system comprising: three-dimensional image-data acquisition means for acquiring three-dimensional image data of a bone structure; three-dimensional image-generation means for generating a three-dimensional image of the bone structure from the said three-dimensional image data; two-dimensional image-data acquisition means for acquiring two-dimensional image data of a or the bone structure with an implant thereon; and registration means for registering the three-dimensional image data and the two-dimensional image data based on bone structure geometry and/or implant geometry to determine an alignment of the said implant with three-dimensional image of the bone structure.

The invention will now be more particularly described, by way of example only, with reference to the accompanying drawings, in which.

Figure 1:
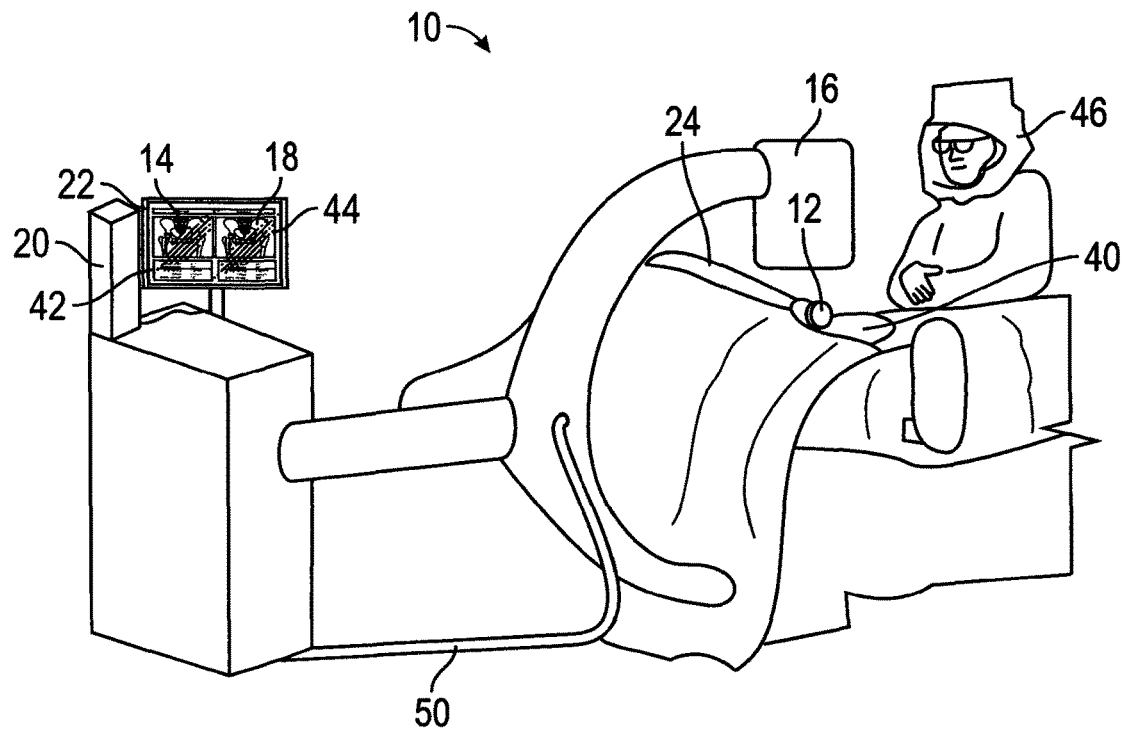
FIG. 1 shows an embodiment of the joint prosthesis and/or trial implant alignment system, in accordance with the first aspect of the present invention, in use.

Firstly, referring to FIG. 1 there is shown a joint prosthesis and/or trial implant alignment system 10 for intraoperatively assisting an alignment of a joint prosthesis and/or trial implant 12 during a surgical procedure. The system 10 comprises patient-specific pre-operative data 14, a patient imaging device 16, patient-specific intraoperative data 18, registration means 20 and a display device 22. It will be appreciated that alignment may include position, orientation and/or placement and therefore may define the alignment of the joint prosthesis and/or trial implant 12 with six degrees of freedom.

The joint prosthesis 12 may be considered to be an artificial element which is to be implanted in or on a patient 24 to either replace or be an addition to the patient's joint, post-operatively. The joint prosthesis 12 may therefore be a long term or permanent implant. The trial implant 12 may also be a removable artificial element implanted in or on the patient 24 to provide an intraoperative indication of alignment, position or size of a or the prosthesis, which may particularly be a or the joint prosthesis 12. The trial implant 12 can as such be considered to be a short term or temporary implant and would not be intended to remain implanted in the patient 24 post-operatively. However, both the joint prosthesis and the trial implant in this current are preferably considered to be implants. The joint prosthesis or trial implant 12 may particularly be an acetabular cup 26, femoral head 28, femoral stem 30, acetabular cup liner, screw, bolts; femoral, tibial and patellar components of a total knee replacement prosthesis; humeral head, glenoid component and/or custom prosthesis and/or trial implant; however, the registration of other prostheses may be feasible.

Although described as a joint prosthesis, it will be appreciated that any other type of prosthesis may be considered for the purposes for this invention, particularly any prosthesis which requires verification of alignment, orientation and/or position relative to the patient's body. For example, a spinal prosthesis and/or an orthopaedic implant may also be considered.

Figure 2:
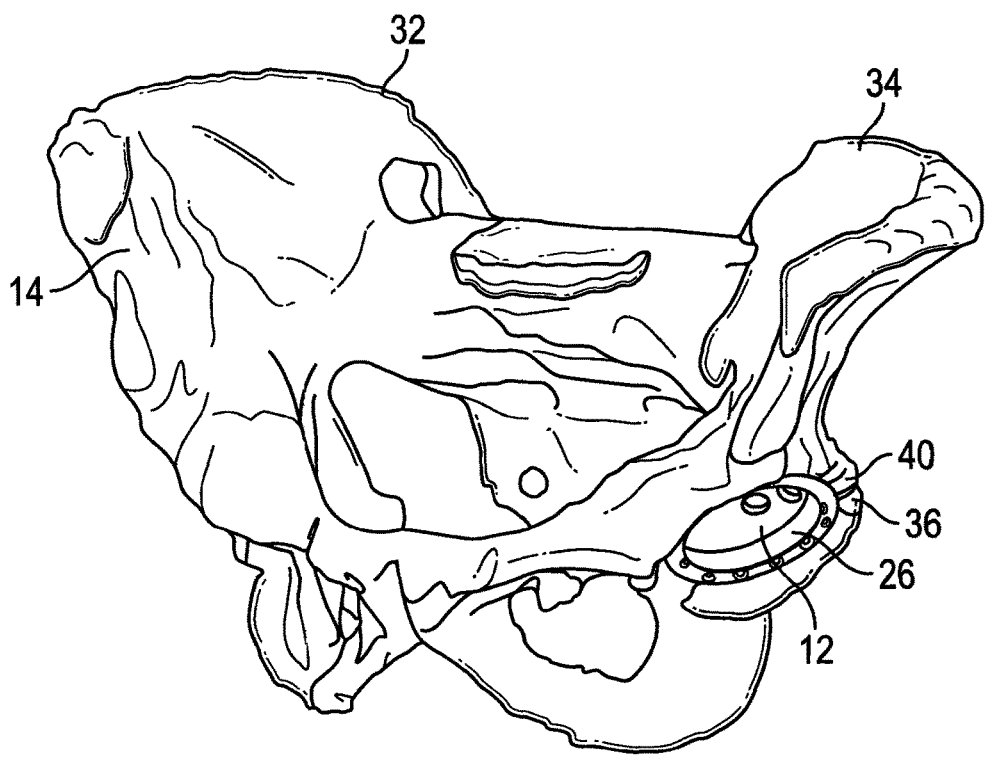
FIG. 2 shows one embodiment of patient-specific pre-operative data of the joint prosthesis and/or trial implant alignment system of FIG. 1, given in three-dimensions.

The patient-specific pre-operative data 14 forms, is used to form, or is formable into a three-dimensional image containing bone structure 32 and preferably a predetermined alignment of the joint prosthesis and/or trial implant 12. The patient-specific pre-operative data 14 may contain the bone structure 32 and/or the predetermined alignment or the three-dimensional image may contain the bone structure 32 and/or the predetermined alignment. Alternatively, the patient-specific pre-operative data 14 may contain the bone structure 32 or the three-dimensional image may contain the bone structure 32. In the instance that the surgical procedure is for a hip joint replacement such as total hip arthroplasty (THA), the patient-specific pre-operative data 14 and/or three-dimensional image may include, for example, a pelvis 34 of the patient 24, an acetabulum 36 of the patient 24 and an acetabular cup prosthesis 26, as shown in FIG. 2. The data and/or image 14 may further or alternatively include a femur 38 of the patient 24 and a femoral head prosthesis 28. The pre-operative data may further include other parts of the patient, for example muscle tissue. The preoperative data 14 may include predetermined numerical values of alignment, for example predetermined angles of anteversion or inclination for an acetabular cup in THA.

The three-dimensional image 14 preferably shows, has or indicates the desired relative position and/or orientation of the joint prosthesis and/or trial implant 12 with respect to the bone structure 32. The three-dimensional image 14 may therefore be considered to show a virtual representation of the joint prosthesis and/or trial implant 12 and/or the bone structure 32. The three-dimensional image 14 may be a model, simulation, representation, graphic, drawing or other type of image.

The pre-operative data 14 may be patient-specific due to the bone structure 32 having a likeness of, being representative of or identical to the bone structure of said patient 24. The bone structure 32 component of the data may therefore be obtained by pre-operatively imaging the patient 24, for example by using an X-ray imaging device, to form single or multi plane X-ray images, ultrasound imaging device, computed tomography scan and/or magnetic resonance imaging scan.

Alternatively, the bone structure 32 component may be obtained by using statistical shape modelling or statistical shape analysis. The bone structure 32 would thereby be obtained by an averaging, combination or amalgamation of dimensions of bone structure of multiple persons having similar or identical characteristics of said patient 24 and/or meeting certain criteria. In this way, the bone structure 32 of the three-dimensional image 14 may not be identical to the bone structure of the patient 24 and/or to bone structure as given in the two-dimensional image 18. If obtained from statistical shape modelling, the pre-operative data 14 may be considered to be patient-specific or patient-class-specific having typical characteristics of the patient.

Alternatively or additionally, the pre-operative data 14 may also be patient-specific due to a patient-specific alignment of the joint prosthesis and/or trial implant 12 with respect to the bone structure 32. For example, in a THA procedure the orientation of the acetabular cup 26 with respect to the acetabulum 36 may be varied for different patients based on patient-specific information which is indicative of one or more dynamic characteristics and post-implant activities preference data. That is, post-operative movement criteria of the patient 24 may determine the predetermined alignment of the joint prosthesis and/or trial implant 12 with respect to the bone structure 32.

Whilst described as forming a three-dimensional image, it will be appreciated that the patient-specific pre-operative data may not form a three-dimensional image which is visible to a user and may instead be a data set which may be manipulated to generate the three-dimensional image. Additionally, it will be appreciated that the patient-specific pre-operative data may in fact be or form a two-dimensional image.

The patient imaging device 16 is suitable for intraoperatively imaging in two dimensions an operative area 40 of the patient 24 and may preferably be an X-ray, fluoroscope, ultrasound, PACS or Therapy Imaging and Model Management System. This is such that the patient imaging device 16 may directly image the bone structure 32 of the patient 24 and/or the joint prosthesis and/or trial implant 12. The patient imaging device 16 optionally provides real-time moving or video intraoperative images of the operative area 40 of the patient 24, particularly in the instance that the patient imaging device 16 is a fluoroscope, although it will be appreciated that this is not necessary to form a two-dimensional image 18.

The operative area 40 of the patient 24 includes at least part of the bone structure 32 being operated on, a surrounding bone structure and/or at least part of the trial prosthesis and/or trial implant 12 being implanted.

It will be appreciated that the above-defined imaging devices 16 may be capable of forming an image showing objects at different relative depths to each other, although these, for purpose of this invention, would be considered to be two-dimensional images 18. Therefore, it will be appreciated that an imaging device 16 that produces a two-dimensional cross-section and an imaging device 16 which produces a two-dimensional image showing objects at different relative depths, may be suitable for the purposes of this invention.

Figure 3:
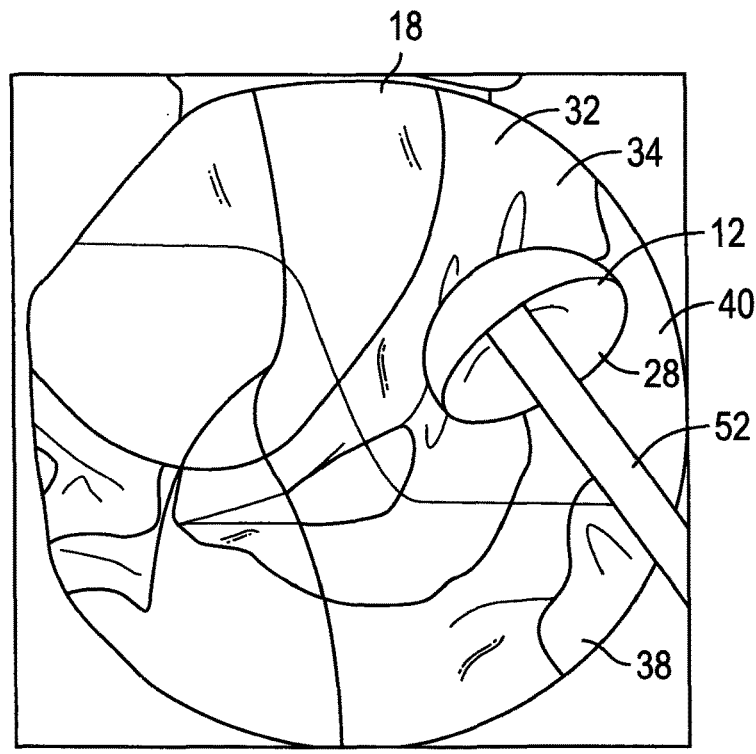
FIG. 3 shows one embodiment of the patient-specific intraoperative data of the joint prosthesis and/or trial implant alignment system of FIG. 1, given in two-dimensions, with an in use implanter.

The patient-specific intraoperative data 18 is outputted from the patient imaging device 16. The patient-specific intraoperative data 18 and/or the patient imaging device 16 forms or is used to form a two-dimensional image 18 showing bone structure 32 and a real-time position or alignment of the joint prosthesis and/or trial implant 12 thereon. Alignment may include the position and/or orientation of the joint prosthesis and/or trial implant 12 relative to the bone structure 32. An example of the patient-specific intraoperative data 18 is shown in FIG. 3.

It will be appreciated that the two-dimensional image 18 may show only a plane or cross-section or may show objects in a foreground and/or background. Whilst the two-dimensional image 18 is described as showing a real-time position or alignment of the joint prosthesis and/or trial implant 12, it will be appreciated that the alignment of the joint prosthesis and/or trial implant 12 relative to the bone structure 32 may not necessarily be continuously updated. Therefore, the real-time position or alignment of the joint prosthesis or trial implant 12 may refer to an intraoperative alignment at a given point during the surgery, which could, unintentionally or otherwise, vary between imaging and registration. However, for the purposes of the invention, the alignment in the two-dimensional image 18 is to be considered to be real-time during the registration process. Whilst the intraoperative data 18 is described as forming a two-dimensional image it will be appreciated that the two-dimensional image may not in fact be visible to the user and therefore there may not in fact be an image as such. Instead the intraoperative data 18 may only be a data set manipulatable to form an image.

The registration means 20 is for registering the intraoperative data 18 with the pre-operative data 14 based on geometry of said bone structure and/or geometry of said joint prosthesis and/or trial implant 12. Said geometries may include at least one of a point, contour, profile, plane, line, curvature or radius of the bone structure 32 and/or the joint prosthesis and/or trial implant 12.

In the instance that the bone structure 32 component of the three-dimensional image 14 has been obtained through imaging, the geometry of the bone structure 32 of the three-dimensional image 14 will be identical or substantially identical to the geometry of the bone structure 32 of the two-dimensional image 18. In the instance that the bone structure 32 component of the three-dimensional image 14 has been obtained through statistical shape modelling or analysis, the geometry of the bone structure 32 of the three-dimensional image 14 may be similar or identical to the two-dimensional image 18. In this way they may not precisely correspond to each other, although it will be appreciated that the geometries may still sufficiently correspond to be registerable with each other for the purposes of the invention.

Similarly, the geometries of the joint prosthesis and/or trial implant 12 may not precisely correspond to each other in the instance that a different implant 12 has been selected to that which was used for predetermination. However, it will be appreciated that the geometries may still sufficiently correspond to be registerable with each other for the purposes of the invention.

The registration means 20 may here include a registration circuit and/or a processor for performing the registration and a memory storage device, which may be onboard the processor, for storing the patient-specific pre-operative data 14, the patient-specific intraoperative data 18 and/or an output of the registration means 20. The registration means 20 may further include or be provided by an electronic device 42, for example a portable electronic device. Said portable electronic device may, for example, be a tablet or a smart-phone.

The registration means 20 and/or registration circuit preferably comprises contouring or contour determination means for determining contouring of bone structure 32 and/or the joint prosthesis and/or trial implant 12 in the patient-specific pre-operative data 14 and/or the patient-specific intraoperative data 18. The contouring determination means is for determining contouring of bone structure 32 and/or joint prosthesis and/or trial implant 12 in the two-dimensional image 18 and/or three-dimensional image 14. The contouring determination means may preferably include or be a contouring determination circuit.

The registration means 20 preferably further includes a landmark designation means for designating a landmark of bone structure 32 and/or joint prosthesis and/or trial implant 12 which is common to the patient-specific intraoperative data 18 and patient-specific pre-operative data 14. The landmark designation means may therefore comprise a means for designating, identifying or marking at least one point, contour, profile, plane, line, curvature or radius of the bone structure 32 and/or the joint prosthesis and/or trial implant 12 on the two-dimensional image 18 and/or three-dimensional image 14.

In this way the landmark designation means may include a user interface 44 and/or image and/or data manipulation means to allow the user, who may be a surgeon 46 or other surgical staff, to interact with the intraoperative data 18, pre-operative data 14, two-dimensional image 18 and/or three-dimensional image 14. Such interaction may include rotating, enlarging, or otherwise altering a view of the three-dimensional image 14 or two-dimensional. The landmark designation means may also include marker positioning means to allow the user to select or mark geometries of the data or images, preferably using the user interface 44. The user interface 44 may include a touch-screen, a computer mouse and/or a keyboard.

Whilst the landmark designation means is described as being manually operable by the user or surgeon 46, it will be appreciated that the landmark designation may be carried out automatically by automated landmark tagging means, such as via an automated image recognition process. The landmark designation may additionally or alternatively be carried out by medical personnel remote from the surgery.

The display device 22 is capable of intraoperatively displaying an output of the registration means 20, thereby enabling a visual indication of the said real-time alignment of the joint prosthesis and/or trial implant 12 relative to the said predetermined alignment. The display device 22 is preferably included as part of said electronic device 42 as described above, although it will be appreciated that there may in fact be a further electronic device 42 to form the display device 22. It will be appreciated that the visual indication may alternatively display the said real-time alignment of the joint prosthesis and/or trial implant relative to the bone structure in the three-dimensional image, if there is an absence of the predetermined alignment.

The output of the registration means 20 preferably includes the two-dimensional image 18 superposed with the three-dimensional image 14. In this way the two-dimensional image 18 overlaid on the three-dimensional image 14, or vice versa, is displayable on the display device 22. The display device 22 may further include a further or the user interface 44 to allow image or data manipulation or movement of the superposed or overlain images 14, 18, either individually or together.

Additionally or alternatively, the output of the registration means 20 may include values or numerical data 48 of real-time orientation and/or positioning of the joint prosthesis and/or trial implant 12 relative to the bone structure 32. The values 48 may be displayable on the display device 22 for in use reference for the surgeon 46. For example, in the instance of THA, an angle of inclination and/or anteversion of the acetabular cup 26 as inserted may be displayed on the display device 22. Additionally, predetermined values of, for example, the above two angles, may also be displayable alongside the real-time values 48 to allow direct comparison between the predetermined and real-time alignments.

Although the orientation and/or positioning is described as "real-time", it will be appreciated that the orientation and/or positioning may not in fact be "real-time" and may in fact be the orientation and/or positioning of the implant 12 at the time of obtaining the patient-specific intraoperative data 18 from the patient imaging device 16.

Furthermore, the output of the registration means 20 may include at least one indicator to indicate a direction and/or magnitude of adjustment to the joint prosthesis and/or trial implant 12 to correspond with the said predetermined alignment. This may especially be provided in the instance that the real-time alignment of the join prosthesis and/or trial implant 12 does not match or correspond to the predetermined alignment. For example, the indicator may therefore include the direction and magnitude of tilt required to have the joint prosthesis correctly aligned. This may take the form of an indicator such as an arrow showing the direction and an accompanying label giving the magnitude of the required movement. The arrow could also be scaled proportionally to be magnitude of the required movement.

Alternatively or additionally, the output of the registration means 20 may include a real-time or pseudo-real-time three-dimensional image 14 produced from a combination of at least part of the patient-specific intraoperative data 18 and/or patient-specific pre-operative data 14. The patient-specific intraoperative data 18 may provide the real-time alignment, position and/or orientation of the implant 12 relative to the bone structure 32. Having obtained the real-time alignment and knowing the geometry of the implant 12 and/or bone structure 32, a further three-dimensional image 14 may be producible which may effectively show the real-time alignment of the implant 12 in three-dimensions. This may be compared to, overlain with, or superposed with the predetermined three-dimensional image 14 to provide an indication of the alignment required.

The alignment system 10 may further comprise a data transferal means 50 for transferring the pre-operative data 14 and intraoperative data 18 to the registration means 20. This data transferal means 50 may include a wired or wireless data connection between the patient imaging device 16 and the registration means 20 for transferring the patient-specific intraoperative data 18 to the registration means 20. This may, for instance take the form of inductors, a Wi-Fi® or Bluetooth® connection.

Additionally or alternatively, the system may further comprise a secondary imaging device for producing an intermediary two-dimensional copy of said two-dimensional image 18 for transferal to the registration means 20. For example, if the imaging device 16 is a fluoroscope, the surgical personnel may produce the copy of the image of the output of the fluoroscope with the secondary imaging device and then transfer this to the registration means 20, via a wired or a wireless connection. In the instance that the registration means 20 includes the portable electronic device 42, the portable electronic device 42 may comprise a camera which may be the secondary imaging device.

In use, to intraoperatively assist an alignment of a joint prosthesis and/or trial implant 12, a required or desired alignment of the joint prosthesis and/or trial implant 12 on the bone structure 32 may be pre-operatively predetermined. This may be determined by the surgeon 46 or other medical personnel and may be based on patient-specific information which is indicative of one or more dynamic characteristics and post-implant activities preference data. That is, post-operative movement criteria of the patient 24 may determine the predetermined alignment of the joint prosthesis and/or trial implant 12.

For example, in the instance of a THA, the angle of inclination and/or anteversion of the acetabular cup 26 with respect to the acetabulum 36 as well as femoral stem 30 length is determined for a given patient 24 based on the range of motion required for the patient 24 post-operatively and/or medical literature.

To accurately predetermine this alignment, the operative area 40 and/or bone structure 32 of the patient 24 is preferably imaged using any of the methods previously discussed and/or the statistically probable shape of the patient's operative area 40 is determined. This additionally assists determining the dimensions of the joint prosthesis and/or trial implant 12 to be implanted.

The alignment of the implant 12, the bone structure 32 of the patient 24 and/or the dimensions of the joint prosthesis preferably forms at least part of the patient-specific pre-operative data 14. Having determined this, the three-dimensional image 14, model or simulation is formed having the virtual representation of the bone structure 32 of the patient 24 or the statistically assumed bone structure 32 of the patient 24 and the implant 12 to be implanted. For THA, the three-dimensional image 14 may include the pelvis 34 and femur 38, as well as the acetabulum 36 and femoral head 28. In the instance that the bone structure 32 is altered during the surgical procedure, for example the head of the femur 38 being removed in THA, this may be included in the three-dimensional image 14 to enable a direct comparison of the real-time and predetermined alignments during the surgical procedure. Therefore, the patient-specific pre-operative data 14 may be considered to include predetermined post-operative bone structure of the patient 24 and/or statistical shape modelled bone structure.

It will be appreciated that as an alternative, the patient-specific pre-operative data may not include data relating to the predetermined alignment of the joint prosthesis and/or trial implant.

Having formed the predetermined three-dimensional image 14, or first image in three dimensions, the patient 24 may undergo the surgical procedure. This would occur in an operating room in the hospital. The surgeon 46 would implant the joint prosthesis and/or trial implant 12 on the actual bone structure 32 of the patient 24. For THA, the surgeon 46 would expose the hip joint of the patient 24 and dislocate the femoral head from the acetabulum 36. The femoral head would be removed and a femoral stem and/or femoral head prosthesis 30, 28 or trial implant would be implanted on the femur 38. The acetabulum 36 would be reamed and an acetabular cup 26 implanted on the acetabulum 36 using an implanter 52. The femoral stem and/or femoral head prosthesis 30, 28 would be inserted into the acetabular cup 26. During this procedure, the surgeon 46 would attempt to initially intraoperatively align the joint prosthesis and/or trial implant 12 with the predetermined alignment via palpation or eye.

Having intraoperatively implanted the joint prosthesis and/or trial implant 12, the surgeon 46 or surgical assistant images the operative area 40 of the patient 24 to obtain the patient-specific two-dimensional image 18 or image data. This acquires second image data 18 in two dimensions of the operative area 40 of the patient 24 relating to said actual bone structure 32 and a real-time position of the joint prosthesis and/or trial implant 12 thereon. The operative area 40 of the patient 24 may be imaged by any of the patient imaging devices 16 as described above. The two-dimensional image 18 may include the implanter 52.

The surgeon 46 may image the operative area 40 from one perspective, direction or position only. Alternatively, the surgeon 46 may image the operative area 40 from multiple perspectives. This allows cross-referencing and so the real-time, actual or intraoperative alignment of the joint prosthesis or trial implant 12 with respect to the bone structure 32 may be obtained more accurately or reliably. This may be extended to imaging the operative area 40 of the patient 24 in three-dimensions to acquire a real-time or actual intraoperative three-dimensional image or image data of the operative area 40 of the patient 24.

The second image data or intraoperative data 18 is then transferred to the registration means 20. This is done via the data transferal means 50 and therefore the image data may automatically be transferred by the wireless or wired data connection. Alternatively, the surgeon 46 or other surgical personnel may image the intraoperative image data with the secondary imaging device and effectively manually transfer the two-dimensional image 18 to the registration means 20. The two-dimensional image 18 may be loaded or stored on the memory device of the electronic device 42 of the registration means 20. The pre-operative data 14 having the three-dimensional image is also loaded or stored on the memory device of the electronic device 42.

Figure 4:
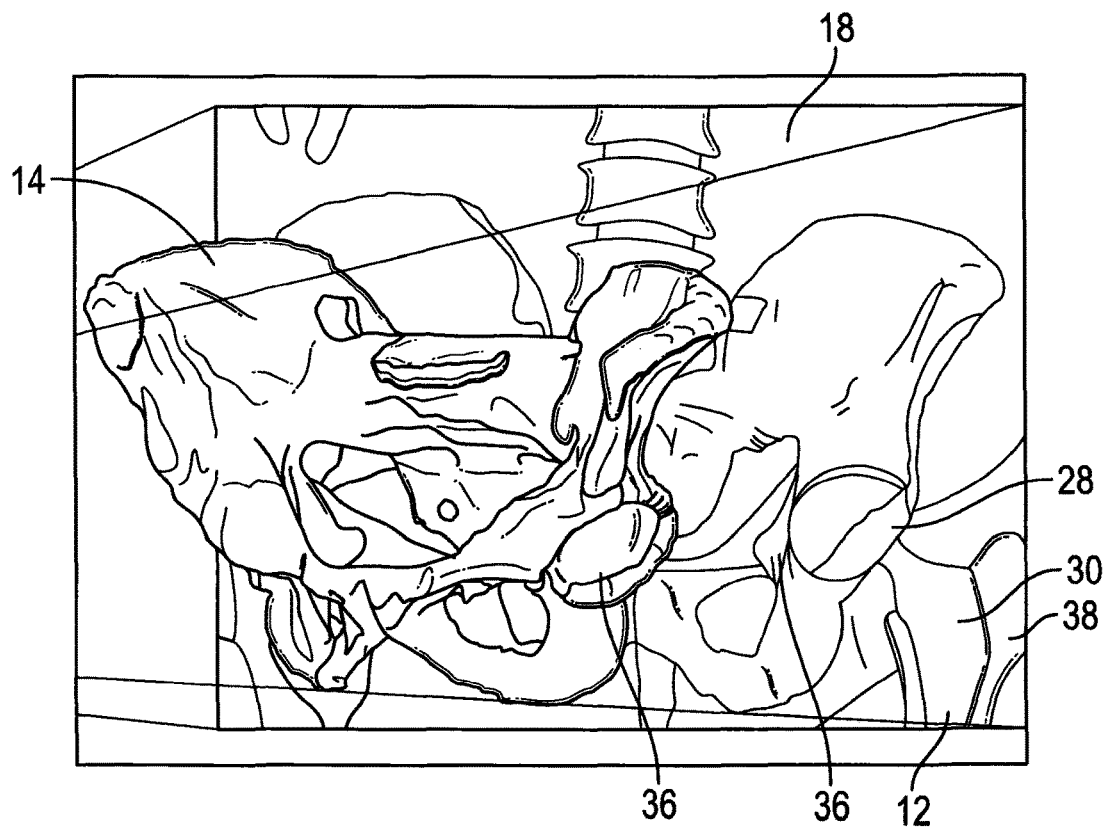
FIG. 4 shows one embodiment of a registration means of the joint prosthesis and/or trial implant alignment system of FIG. 1, showing registration of the patient-specific intraoperative data with the patient-specific pre-operative data of FIG. 2.

The registration means 20 then preferably registers the two-dimensional and three-dimensional images 18, 14. This registration is done by matching common geometries of the two-dimensional and three-dimensional images 14, which is undertaken via the processor of the registration means 20. A representation of the registration process is shown in FIG. 4.

The real-time or intraoperative geometry, or at least a part of the geometry, of the bone structure 32 and/or joint prosthesis and/or trial implant 12 of the two-dimensional image 18 is first identified or determined. The identification of geometry of the two-dimensional image 18 is preferably done via the contouring determination means identifying contouring of the bone structure 32 and/or implant 12. This may be most accurately or simply determined from at least part of an outline or outlines of the bone structure 32 and/or implant 12, although it will be appreciated that the contouring may be determined from a surface of the bone structure 32 or implant 12. It will be appreciated that registration or contouring determination may be performed with respect to parts of the femur, including the lesser trochanter, greater trochanter, resection level and/or greater trochanter; parts of the pelvis, including the anterior superior iliac spine, acetabular teardrop, obturator foramen, iliac crest, anterior inferior iliac spine, pubic symphysis and/or ischial tuberosity; parts of the stem of the femoral implant, including the stem shoulder, stem tip, head centre and/or stem axis; and/or parts of the cup, including the cup centre, cup rim and/or cup apex.

After identifying the contouring of the two-dimensional image 18, the registration means 20 or contouring determination means may then attempt to identify similar, identical or common contouring in the three-dimensional image 14 or pre-operative data 14. If such contouring is found, the perspective from which the two-dimensional image 18 was taken can be identified. The pre-operative data 14 and the intraoperative data 18 can therefore be directly compared and/or contrasted.

This process may be considered to be, or be similar to, rotating the three-dimensional image 14 until the geometry of the bone structure 32 or implant 12 of the three-dimensional image 14 matches that of the two-dimensional image 18.

Whilst the registration means 20 is described as determining the contouring or geometry of the two-dimensional image 18 before the three-dimensional image 14, it will be appreciated that this process may be reversed. Whilst described as identifying contours, it will be appreciated that the registration means may identify common lines, planes, curvatures, radii, profiles or points between the pre-operative and intraoperative data. A common point may be defined by its position with respect to other parts of the bone structure, implant, or other parts of the patient, for example muscle tissue. The aforementioned indicators of common geometry may be registered either separately or in combination.

This registration means 20 preferably occurs automatically, without requiring input from the surgeon 46 or surgical assistant. However, in the instance that the registration means 20 is unable to automatically determine common geometries between the intraoperative data 18 and the pre-operative data 14, it will be appreciated that the surgeon 46 or surgical assistant may use landmark designation means to assist with registration. In this instance the user, the surgeon 46 or surgical assistant would analyse the two-dimensional and three-dimensional images 18, 14 and visually identify any common geometries. The user would then use the user interface 44 to position at least one marker on or select at least one area of the two-dimensional image 18. The user would then do the same at a corresponding position on the three-dimensional image 14. Having designated these landmarks and thereby narrowing the number of possible common geometries, the processor may be able to register the two images together.

Whilst this landmark designation means is described as being utilised only when the registration means 20 is unable to register the two images, it will be appreciated that the landmark designation means may instead be routinely used to more efficiently or with a greater chance of success, register the two images together.

Additionally or alternatively, the registration means 20 and/or the landmark designation means may utilise principles of geometric morphometrics. Preoperatively or intraoperatively, landmarks or positions of interest, for example positions or points of significant changes in curvature or gradient of contours or lines, may be identified on the three-dimensional image 18. This may be carried out manually or automatically. Intraoperatively, the same process may be done on the two-dimensional image 14. The registration means 20 may then intraoperatively attempt to identify common geometric morphometric positions or points between the two images 14, 18, either in combination with or instead of the images 14, 18.

Furthermore, the user, surgeon or surgical assistant may input data, such as numerical data, to assist the registration means. This numerical data may take the form of dimensions of the implant, for example the radius, diameter or size of an acetabular cup.

Having registered or referenced the two-dimensional data 18 to or with the three-dimensional data 14, the output of this registration means 20 is then intraoperatively displayed on the display device 22, which as described before may be the electronic device 42 which acts or comprises the registration means 20. One example of displaying the output of the registration means 20 is to first display the intraoperative two-dimensional image 18 on the electronic display device 22. Having previously found the perspective from which the two-dimensional image 18 was taken, the three-dimensional image 14 is rotated so that it is displayed to the surgeon 46 from this perspective. The two-dimensional image 18 and the three-dimensional image 14 may then be superposed with each other to clearly show any difference between the two images, thus showing any required adjustment to allow the intraoperative alignment to correspond to the pre-operatively predetermined alignment. This superposition may take the form of overlaying an outline, from the determined perspective, of the three-dimensional image 14 on the two-dimensional image 18. Alternatively, the three-dimensional image 14, rotated or oriented to appear as being viewed from said perspective, may be formatted so that it is partially transparent and then overlain on the two-dimensional image 18. It will be appreciated that alternatively an outline or partially transparent format of the two-dimensional image 18 may be overlain on the three-dimensional image 14.

Figure 5:
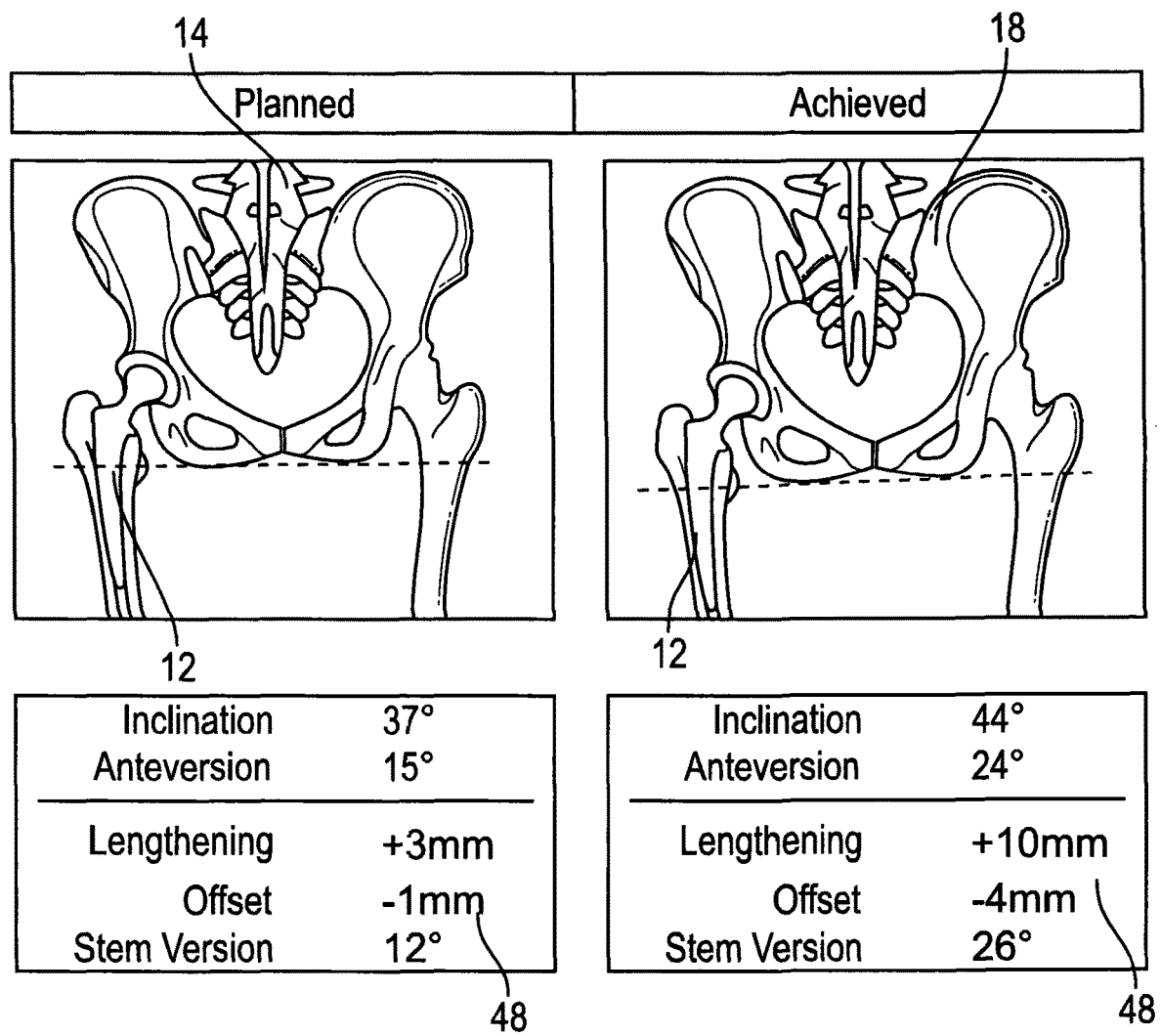
FIG. 5 shows an output of the registration means on a display device of the joint prosthesis and/or trial implant alignment system of FIG. 1.

Instead of superposing the two images, the two images may instead be labelled and displayed adjacent to each other on the display device 22, thereby allowing direct comparison as shown in FIG. 5.

Additionally or alternatively, values 48 of alignment, orientation or position of the real time arrangement of the joint prosthesis and/or trial implant 12 relative to the bone structure 32 may be determined. Said values 48 may be determined by identifying the bone structure 32 and the implant 12 in the intraoperative data 18, for example via identifying common geometry and/or contouring between the two-dimensional and three-dimensional as described previously. Having identified the locations of these two elements, their relative alignment can be defined numerically. For example, in the instance of a THA, having determined the relative orientation of the acetabular cup 26 with the acetabulum 36, the real-time angles of inclination and anteversion can be found or computed.

This computation may be done with respect to the three-dimensional image 14, for example with the angular difference between the two alignments equating to a difference in the real-time and predetermined angles of inclination and anteversion. Alternatively, this computation may be possible to be carried out only with the alignment provided by the two-dimensional image 18. An example value of real-time inclination may be 44°, of predetermined inclination may be 37°, of real-time anteversion may be 24° and of predetermined anteversion may be 15°. Values of leg lengthening, for example a real-time value of +10 mm and a predetermined value of +3 mm; femoral offset, for example a real-time value of −4 mm and a predetermined value of −1 mm; and stem version, for example a real-time value of 26° and a predetermined value of 12°, may also be identified and displayed.

The predetermined and/or real-time values 48 of alignment, orientation or position, and any difference therebetween, may be displayed on the display device 22. This provides indication to the surgeon 46 of the extent to which the two alignments match. Alternatively or additionally, indicators or instructions, as previously described, may be displayed on the display device 22 to inform or guide the surgeon 46 to the correct adjustment required.

Once the output of the registration means 20 has been intraoperatively displayed to the surgeon 46, the surgeon 46 is able to intraoperatively verify whether the real-time alignment of the joint prosthesis and/or trial implant 12 corresponds to the predetermined alignment. If the real-time alignment does not correspond to the predetermined alignment and/or the real-time alignment is not within an acceptable range of the predetermined alignment, the surgeon 46 can intraoperatively adjust the position and/or orientation of the joint prosthesis and/or trial implant 12.

The surgeon 46 can attempt to adjust the implant 12, using the output of the registration means 20 as a guide. This would involve moving the implant 12 in the direction and with the magnitude which is indicated by display device 22. Having adjusted the real-time alignment of the implant 12 with respect to the bone structure 32, the surgeon 46 may then choose to again image the operative area 40 with the patient imaging device 16 and use the registration means 20 and display device 22 to verify the adjusted real-time alignment. Should the adjusted real-time alignment still not correspond to the predetermined alignment and/or the adjusted real-time alignment still not be within an acceptable range of the predetermined alignment, the surgeon 46 may repeat the above process.

It will be appreciated that if the pre-operative three-dimensional image does not contain data relating to a predetermined alignment, then the surgeon may still be able to intraoperatively verify whether the real-time alignment of the joint prosthesis and/or trial implant is optimally positioned with respect to the three-dimensional image of the bone structure.

Whilst the above in use method is described for intraoperatively assisting the alignment of a joint prosthesis or trial implant 12, it will be appreciated that the initially described system may be utilised for other methods. For instance, the system may not be used intraoperatively and may instead be used post-operatively.

For example, the joint prosthesis and/or trial implant 12 may be implanted during surgery. At a given point after surgery, for example as part of a monitoring programme, a routine review or if the patient 24 experiences post-operative issues with the implant 12, a medical practitioner may wish to find a post-operative alignment of the implant 12. Additionally or alternatively, the medical practitioner may wish to determine whether the implant 12 was correctly implanted or whether the implant 12 has been inadvertently repositioned since the surgery. Therefore, the medical practitioner may utilise the aforementioned system to image the former operative area 40 of the patient 24 and obtain a post-operative two-dimensional image 18. This image may be referenced with the patient-specific pre-operative data 14 or patient-specific intraoperative data 18 to indicate whether the implant 12 had been optimally implanted. Even if the medical practitioner determines post-operatively that the implant is misaligned, the medical practitioner may take no further action. Therefore, this method may be for research, academic or statistical purposes only. Alternatively, the medical practitioner may decide that revision surgery is required.

It is therefore possible to provide a joint prosthesis and/or trial implant alignment system for intraoperatively assisting an alignment of a joint prosthesis and/or trial implant during a surgical procedure, without requiring the surgeon to manually verify the alignment. Greater correspondence with the predetermined alignment and so improved post-operative outcomes are therefore possible. The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. A joint prosthesis and/or trial implant alignment system (10) for intraoperatively assisting an alignment of a joint prosthesis and/or trial implant (12) during a surgical procedure, the system (10) comprising:
   a patient imaging device (16) for intraoperatively imaging in two dimensions an operative area of the patient;
   registration circuitry (20) configured to register patient-specific intraoperative data (18) received from the patient imaging device (16) forming a two-dimensional image showing bone structure (32) and a real-time position of a joint prosthesis and/or trial implant (12) thereon with patient-specific pre-operative data (14) forming a three-dimensional image containing bone structure (32) and a predetermined alignment of the joint prosthesis and/or trial implant (12) thereon based on geometry of said bone structure (32) and/or geometry of said joint prosthesis and/or trial implant (12), and enable a visual indication of real-time alignment of the joint prosthesis and/or trial implant (12) relative to said predetermined alignment; and
   a display device (22) configured to intraoperatively display an output of the registration circuitry's visual indication of real-time alignment of the joint prosthesis and/or trial implant (12) relative to said predetermined alignment.

2. A joint prosthesis and/or trial implant alignment system (10) as claimed in claim 1, wherein the geometry of said bone structure and/or geometry of said joint prosthesis and/or trial implant (12) includes at least one of a point, contour, profile, plane, line, curvature or radius.

3. A joint prosthesis and/or trial implant alignment system (10) as claimed in claim 2, wherein the registration circuitry (20) includes contouring determination circuitry for determining contouring of at least one of bone structure, the joint prosthesis and trial implant (12) in the patient-specific intraoperative data (18) and/or patient-specific pre-operative data (14).

4. A joint prosthesis and/or trial implant alignment system (10) as claimed in claim 3, wherein the contouring determination circuitry is configured to determine contouring of at least one of the bone structure, the joint prosthesis and trial implant (12) in the two-dimensional image and/or three-dimensional image.

5. A joint prosthesis and/or trial implant alignment system (10) as claimed in claim 1, wherein the registration circuitry (20) includes contouring determination circuitry for determining contouring of at least one of bone structure, the joint prosthesis and trial implant (12) in the patient-specific intraoperative data (18) and/or patient-specific pre-operative data (14).

6. A joint prosthesis and/or trial implant alignment system (10) as claimed in claim 5, wherein the contouring determination circuitry is configured to determine contouring of at least one of the bone structure, the joint prosthesis and trial implant (12) in the two-dimensional image and/or three-dimensional image.

7. A joint prosthesis and/or trial implant alignment system (10) as claimed in claim 1, wherein the registration circuitry (20) includes landmark designation circuitry for designating a landmark of at least one of the bone structure (32), joint prosthesis, and trial implant (12) that is common to both the patient-specific intraoperative data (18) and patient-specific pre-operative data (14).

8. A joint prosthesis and/or trial implant alignment system (10) as claimed in claim 7, wherein the landmark designation circuitry is configured to designate at least one of the landmark of bone structure (32), joint prosthesis and trial implant (12) that is common to the two-dimensional image and three-dimensional image or a further landmark of bone structure (32), joint prosthesis and trial implant (12) that is common to the two-dimensional image and three-dimensional image.

9. A joint prosthesis and/or trial implant alignment system (10) as claimed in claim 1, wherein said output of the registration circuitry (20) includes the two-dimensional image superimposed on the three-dimensional image or the three-dimensional image superimposed on the two-dimensional image.

10. A joint prosthesis and/or trial implant alignment system (10) as claimed in claim 1, wherein said output of the registration circuitry (20) includes real-time orientation and/or positioning numerical data of the joint prosthesis and/or trial implant (12) relative to the bone structure (32) and/or the predetermined alignment.

11. A joint prosthesis and/or trial implant alignment system (10) as claimed in claim 1, wherein said output of the registration circuitry (20) includes at least one indicator to indicate a direction and/or magnitude of adjustment to the joint prosthesis and/or trial implant (12) to correspond with said predetermined alignment.

12. A joint prosthesis and/or trial implant alignment system (10) as claimed in claim 1, wherein said output of the registration circuitry (20) includes a real-time or pseudo-real-time three-dimensional image produced from a combination of at least part of the patient-specific intraoperative data (18) and/or patient-specific pre-operative data (14).

13. A joint prosthesis and/or trial implant alignment system (10) as claimed in claim 1, wherein the patient imaging device (16) includes at least one of a fluoroscope, X-ray machine, ultrasound, PACS or Therapy Imaging and Model Management System.

14. A joint prosthesis and/or trial implant alignment system (10) as claimed in claim 1, further comprising a wired or wireless data connection (50) between the patient imaging device (16) and the registration circuitry (20) for transferring the patient-specific intraoperative data (18) to the registration circuitry (20).

15. A joint prosthesis and/or trial implant alignment system (10) as claimed in claim 1, further comprising a secondary imaging device for producing an intermediate copy of said two-dimensional image for transferal to the registration circuitry (20).

16. A joint prosthesis and/or trial implant alignment system (10) as claimed in claim 1, wherein the patient-specific pre-operative data (14) is at least in part received from at least one of single-plane X-ray, multi-plane X-ray, magnetic resonance imaging, computer tomography, ultrasound or statistical shape modelling.

17. A joint prosthesis and/or trial implant alignment system (10) as claimed in claim 1, wherein the predetermined alignment of the joint prosthesis and/or trial implant (12) is based on patient-specific information which is indicative of one or more dynamic characteristics and post-implant activities preference data.

18. A joint prosthesis and/or trial implant alignment system (10) as claimed in claim 1, wherein the joint prosthesis and/or trial implant (12) includes an acetabular cup (26), acetabular cup liner, femoral head (28), femoral stem (30), screw, bolts; femoral, tibial and patellar components of a total knee replacement prosthesis; humeral head, glenoid component and/or custom prosthesis and/or trial implant.

19. A joint prosthesis and/or trial implant alignment system for intraoperatively assisting an alignment of a joint prosthesis and/or trial implant during a surgical procedure, the system comprising:
  a patient imaging device for intraoperatively imaging in two dimensions an operative area of the patient;
  registration circuitry configured to
    register patient-specific intraoperative data received from the patient imaging device forming a two-dimensional image showing bone structure and a real-time position of a joint prosthesis and/or trial implant thereon with patient-specific pre-operative data forming a three-dimensional image containing bone structure and a predetermined alignment of the joint prosthesis and/or trial implant thereon based on geometry of said bone structure and/or geometry of said joint prosthesis and/or trial implant, wherein said geometry includes at least one of a point, contour, profile, plane, line, curvature or radius, and wherein the predetermined alignment of the joint prosthesis and trial implant is based on patient-specific information which is indicative of one or more dynamic characteristics and post-implant activities preference data,
    determine contouring of bone structure, the joint prosthesis and trial implant in the patient-specific intraoperative data, patient-specific pre-operative data, and the joint prosthesis and trial implant in the two-dimensional image and/or three-dimensional image,
    designate a landmark of the bone structure, the joint prosthesis, the trial implant that is common to both the patient-specific intraoperative data and the patient-specific pre-operative data, and the joint prosthesis and trial implant that is common to the two-dimensional image and the three-dimensional image,
    indicate a direction and magnitude of adjustment to the joint prosthesis and trial implant to correspond with the predetermined alignment,
    output the two-dimensional image superimposed on the three-dimensional image or the three-dimensional image superimposed on the two-dimensional image,
    output real-time orientation and positioning numerical data of the joint prosthesis and trial implant relative to the bone structure and the predetermined alignment, and
    output a real-time or pseudo-real-time three-dimensional image produced from a combination of patient-specific intraoperative data and patient-specific pre-operative data;
  a wired or wireless data connection between the patient imaging device and the registration circuitry for transferring the patient-specific intraoperative data to the registration circuitry;
  a secondary imaging device for producing an intermediate copy of said two-dimensional image for transferal to the registration circuitry; and
  a display device configured to intraoperatively display an output of the registration circuitry, thereby enabling a visual indication of real-time alignment of the joint prosthesis and/or trial implant relative to the predetermined alignment.

* * * * *